(12) United States Patent
Yoon et al.

(10) Patent No.: US 11,579,131 B2
(45) Date of Patent: Feb. 14, 2023

(54) DETACHABLE DEVICE FOR REPEATEDLY MEASURING TEXTURAL CHARACTERISTICS OF FOOD AND SYSTEM FOR REPEATEDLY MEASURING TEXTURAL CHARACTERISTICS OF FOOD

(71) Applicant: KNU-INDUSTRY COOPERATION FOUNDATION, Chuncheon-si (KR)

(72) Inventors: Won-Byong Yoon, Chuncheon-si (KR); Yun-Ju Lee, Jecheon-si (KR); Hwa-Bin Jung, Gangneung-si (KR)

(73) Assignee: KNU-INDUSTRY COOPERATION FOUNDATION, Chuncheon-si (KR)

( * ) Notice: Subject to any disclaimer, the term of this patent is extended or adjusted under 35 U.S.C. 154(b) by 555 days.

(21) Appl. No.: 16/620,239

(22) PCT Filed: Nov. 1, 2018

(86) PCT No.: PCT/KR2018/013143
§ 371 (c)(1),
(2) Date: Dec. 6, 2019

(87) PCT Pub. No.: WO2020/004725
PCT Pub. Date: Jan. 2, 2020

(65) Prior Publication Data
US 2022/0003734 A1    Jan. 6, 2022

(30) Foreign Application Priority Data

Jun. 29, 2018  (KR) .................. 10-2018-0075395
Jun. 29, 2018  (KR) .................. 10-2018-0075412

(51) Int. Cl.
*G01N 3/28*    (2006.01)
*G01N 3/08*    (2006.01)
(Continued)

(52) U.S. Cl.
CPC .............. *G01N 33/02* (2013.01); *G01N 3/02* (2013.01)

(58) Field of Classification Search
CPC ............ G01N 33/02; G01N 3/02; G01N 3/54; G01N 1/04; G01N 29/2418; G01N 1/14;
(Continued)

(56) References Cited

U.S. PATENT DOCUMENTS

2016/0327537 A1\*  11/2016  Park ...................... G01N 33/02

FOREIGN PATENT DOCUMENTS

JP    2001-021474 A      1/2001
JP    2001021474 A   \*  1/2001
(Continued)

*Primary Examiner* — Brandi N Hopkins
(74) *Attorney, Agent, or Firm* — Sughrue Mion, PLLC (57) ABSTRACT

Disclosed is a detachable device for repeatedly measuring textural characteristics of food. To this end, the present invention includes: a fixing unit having a probe guide member having, at a center thereof, a predetermined guide hole, having therein a predetermined space, and extending downward; a cylindrical probe configured to move upward and downward while surrounding the probe guide member and having multiple holes formed in a lower surface thereof so that a part of food is extracted in accordance with a degree of compression at the time of compressing the food; a food sample cup positioned below the cylindrical probe and having therein a space in which the food is placed; and multiple position fixing guides positioned between the fixing unit and the food sample cup.

14 Claims, 9 Drawing Sheets

(51) Int. Cl.
*G01N 3/02* (2006.01)
*G01N 33/02* (2006.01)

(58) Field of Classification Search
CPC .... A47J 43/0716; A47J 43/0722; A47J 44/00;
A47J 36/2433; A47J 47/10; A47J
36/2483; A47J 31/4492; A47G 19/22;
B09B 3/00; A23G 9/228; G01K 1/146;
A23L 19/18; G09B 19/0092; G05B
19/048; A23P 20/20; A61B 5/4854
See application file for complete search history.

(56) References Cited

FOREIGN PATENT DOCUMENTS

| | | | |
|---|---|---|---|
| JP | 2003-114218 A | | 4/2003 |
| JP | 2003114218 A | * | 4/2003 |
| JP | 2016-133460 A | | 7/2016 |
| KR | 10-2016-0089753 A | | 7/2016 |
| KR | 10-2017-0142780 A | | 12/2017 |

* cited by examiner

| Initialize | | |
|---|---|---|
| Test speed | | mm/s |
| Deformation | | % |
| Cycle(s) | | |
| Trigger load | | g |
| File name | | |

Measure

[FIG. 14]

| Initialize | | |
|---|---|---|
| Test speed | | mm/s |
| Deformation | | % |
| Cycle(s) | | |
| Trigger load | | g |
| File name | | |

Measure

[FIG. 15]

| | Initialize | |
|---|---|---|
| Test speed | [____] | mm/s |
| Deformation | [____] | % |
| Cycle(s) | [____] | |
| Trigger load | [____] | g |
| File name | [____] | |

Measure

[FIG. 16]

| | Initialize | |
|---|---|---|
| Test speed | [____] | mm/s |
| Deformation | [____] | % |
| Cycle(s) | [____] | |
| Trigger load | [____] | g |
| File name | [____] | |

Measure

[FIG. 17]

DETACHABLE DEVICE FOR REPEATEDLY MEASURING TEXTURAL CHARACTERISTICS OF FOOD AND SYSTEM FOR REPEATEDLY MEASURING TEXTURAL CHARACTERISTICS OF FOOD

CROSS REFERENCE TO RELATED APPLICATIONS

This application is a National Stage of International Application No. PCT/KR2018/013143 filed Nov. 1, 2018, claiming priority based on Korean Patent Application No. 10-2018-0075395, filed Jun. 29, 2018 and Korean Patent Application No. 10-2018-0075412, filed Jun. 29, 2018, the entire disclosures of which are incorporated herein by reference.

TECHNICAL FIELD

The present invention relates to a detachable device for repeatedly measuring textural characteristics of food and a system for repeatedly measuring textural characteristics of food.

BACKGROUND ART

There are various types of food such as a solid type, a liquid type, a semisolid type, a paste type, a type in which particles are dispersed into a liquid, an intermediate type, or a type made of particles.

Figure 1:
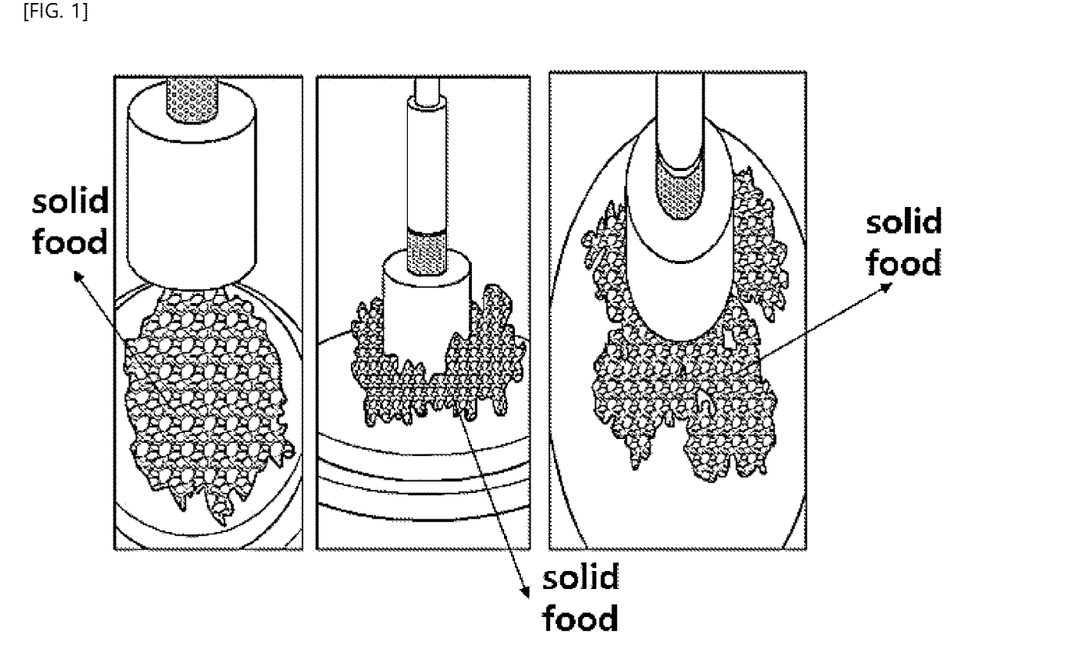
FIG. 1 is a photograph illustrating some constituent elements of a device for measuring textural characteristics of food in the related art.

Meanwhile, as illustrated in FIG. 1, a device for measuring textural characteristics of food in the related art applies a predetermined force to solid food having a certain shape and ascertains, by means of a force value, a degree of deformation inside the food.

However, the device in the related art cannot measure paste food or food that does not maintain a certain shape thereof because this food has a high degree of deformation.

That is, the mastication needs to be performed to repeatedly measure textural characteristics of food having the same volume. Because the food illustrated in FIG. 1 has a high degree of deformation even though the mastication is performed once, the volume or the degree of deformation of the food, which is maintained when the previous mastication is performed, is not maintained when the same mastication is performed once again, and as a result, it is difficult to accurately measure textural characteristics of food.

In addition, because a liquid having particles cannot be measured even by a viscometer, it is difficult to measure textural characteristics and physical characteristics of a certain group of food.

Figure 2:
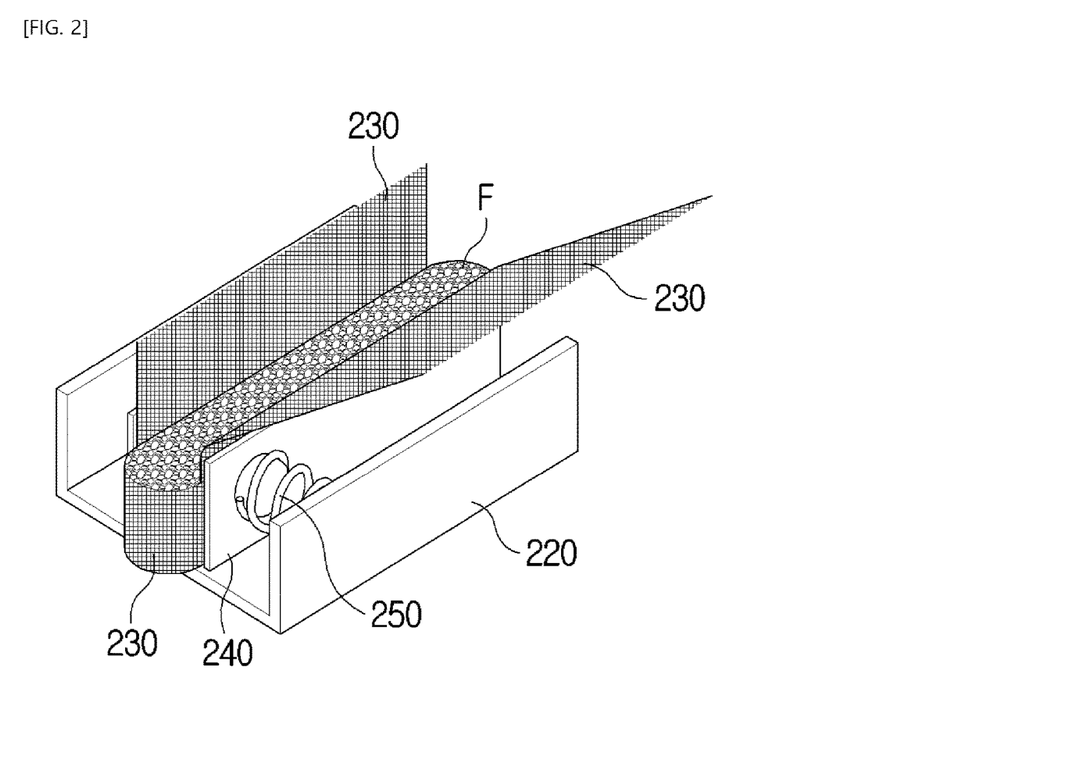
FIG. 2 is a partial configuration view of the invention filed by the present applicant.

In consideration of this situation, the present applicant has filed an application related to a structure in which food (cooked rice) is surrounded by a guide unit 230, as illustrated in FIG. 2.

The guide unit 230 may prevent the food from being withdrawn to the outside during the process of reproducing the mastication.

In addition, a pair of plates 240 capable of applying tension to the food is connected with elastic units 250, and the food is consistently collected inward by the elastic units 250 and the plates 240 during the process of reproducing the mastication, such that a process most similar to the process in which a human actually masticates is implemented.

However, the above-mentioned process is related to the device for reproducing a process most similar to the actual human mastication, but the process is not enough to evaluate inherent physical properties of the food itself instead of the reproduction of the human mastication.

DISCLOSURE

Technical Problem

An object of the present invention is to provide a device having high reproducibility and being capable of measuring textural characteristics of food regardless of physical properties of the food by applying an environment inside a human oral cavity and by using a 'texture analyzer' for measuring textural characteristics of food used in the related art so that the device according to the present invention is attachable to and detachable from the texture analyzer.

In addition, another object of the present invention is that the present device is easily attached to the 'texture analyzer' and then used, such that it is possible to apply a degree of deformation similar to the human mastication to reproduce the mastication in the oral cavity, and it is possible to perform the reproduction of the mastication while changing the number of times of the mastication in accordance with the food.

In addition, still another object of the present invention is to provide a detachable device for repeatedly measuring textural characteristics of food, the device having a new structure, being capable of measuring physical properties of all types of food such as a solid type, a paste type, a semisolid type, a liquid type regardless of physical properties of the food, and being capable of applying the actual human mastication process by providing a system for measuring textural characteristics, the system having a new structure in accordance with effects of a temperature and saliva in the oral cavity.

Technical Solution

Disclosed is a detachable device for repeatedly measuring textural characteristics of food.

To this end, the present invention includes a fixing unit having a probe guide member having, at a center thereof, a predetermined guide hole, having therein a predetermined space, and extending downward, a cylindrical probe configured to move upward and downward while surrounding the probe guide member and having multiple holes formed in a lower surface thereof so that a part of food is extracted in accordance with a degree of compression at the time of compressing the food, a food sample cup positioned below the cylindrical probe and having therein a space in which the food is placed, and multiple position fixing guides positioned between the fixing unit and the food sample cup.

Advantageous Effects

According to the present invention having the above-mentioned configuration, the following effects are implemented.

(1) There is an advantage in that a user may easily attach some configurations of the present invention to a mastication reproduction apparatus (texture analyzer) in the related art.

(2) A device for compressing the food in the related art masticates the food in a state in which there is no hole through which a part of the food is extracted when the food is compressed, and as a result, there is a lack of accuracy according to the repeated reproduction.

For this reason, the food is masticated in a state in which a part of the food is completely withdrawn, and as a result, there is a problem in that it is impossible to repeatedly masticate the food having the same volume.

However, according to the present invention, there is an advantage in that it is possible to repeatedly reproduce the mastication of the food having the same volume several times.

(3) It is possible to repeat the mastication of the food and perform the mastication of the food having the same volume for each repeated mastication, such that precise results and reproducibility are achieved.

(4) In the related art, the mastication reproduction was possible to some extent in respect to solid food.

However, in the case of food such as paste, it is difficult to repeatedly reproduce the mastication because a part of the food is extracted by one mastication.

In contrast, according to the present invention, there is an advantage in that a fixed volume of paste is consistently maintained, such that the repeated reproduction is excellent.

(5) There is an advantage in that the characteristics of the food itself may be measured more precisely.

(6) There is an advantage in that it is possible to measure not only solid food, but also paste, semisolid, and liquid food, and it is possible to perform the mastication of food with a high degree of deformation similar to that in the oral cavity and thus to measure the textural characteristics generated when a person actually masticates the food.

(7) According to the present invention, there is an advantage in that with the combination of additional devices, it is helpful to implement the desired food by ascertaining the degree of change of the food in accordance with the number of times of the mastication through a graph indicating forces (loads) measured over time.

Further, there is an advantage in that the force and the time may be provided when the textural characteristics of food are not changed no longer by the sufficient mastication.

(8) In the case of using the present invention, with the combination of additional devices, sufficient data may be provided in food research through a graph indicating forces (loads) over time.

Further, there is an advantage in developing the food having desired physical properties by using the present invention during food development, and there is an advantage in that a load (force) value generated in each mastication cycle is displayed in real-time to help an operator recognize the physical properties of the food.

(9) There is an advantage in that the water having a preset temperature and artificial saliva are supplied to sufficiently apply the environment in the oral cavity of the person. After the mastication is performed every time, the food, which is masticated with a high degree of deformation, is moved back to the position set before the mastication, such that the repeated mastication action actually occurring in the oral cavity is reproduced, and thus there is an advantage in that a continuous change in physical properties generated during the mastication of the food may be measured.

(10) The artificial saliva makes it possible to measure not only physical deformation but also changes occurring in the oral cavity by checking the change in textural characteristics caused by an enzymatic reaction. There is an advantage in that among the various probes, a suitable probe may be selected for measuring shearing force or compressive stress in accordance with the physical properties of the food.

(11) The shearing force, the compressive stress, and the food size are simultaneously changed, and as a result, it is possible to analyze complex phenomena that can occur in the oral cavity, and to observe changes in physical properties when various types of food with various physical properties are mixed by the mastication.

MODES OF THE INVENTION

Hereinafter, exemplary embodiments of a detachable device for repeatedly measuring textural characteristics of food and a system for repeatedly measuring textural characteristics of food according to the present invention will be described with reference to the accompanying drawings.

Prior to the description of the present invention, the Korean patent application No. 10-2017-0162847 (System for Reproducing Mastication) previously filed by the present applicant will be briefly described below to help understand the present invention. Meanwhile, reference numerals in the following contents are determined by being restricted to reference numerals in FIG. 3, and the reference numerals may be different from the reference numerals according to the present invention to be described below.

However, the same reference numerals are used for the constituent elements employed identically in the previously filed invention.

Figure 3:
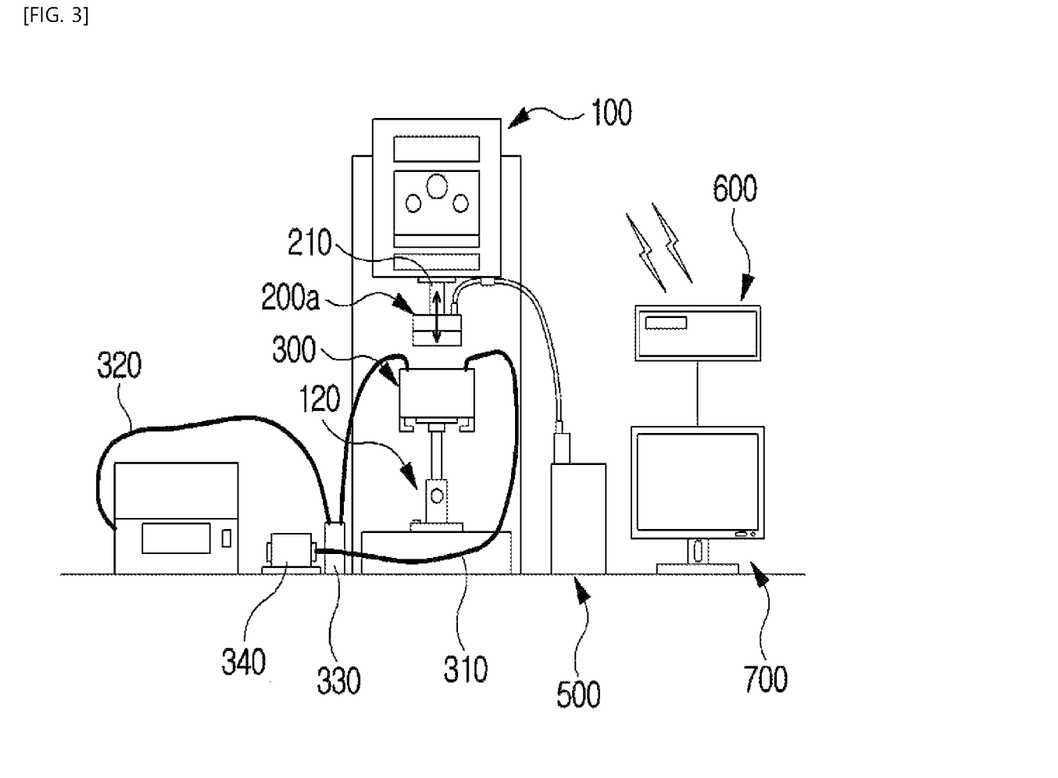
FIG. 3 is an entire configuration view of the invention filed by the present applicant.

As illustrated, the previously filed invention broadly includes a main body 100, an upper tooth probe 200a, a temperature maintaining unit 300, a constant-temperature bath 400, an artificial saliva supply unit 500, a control unit 600, and a display unit 700.

Figure 12:
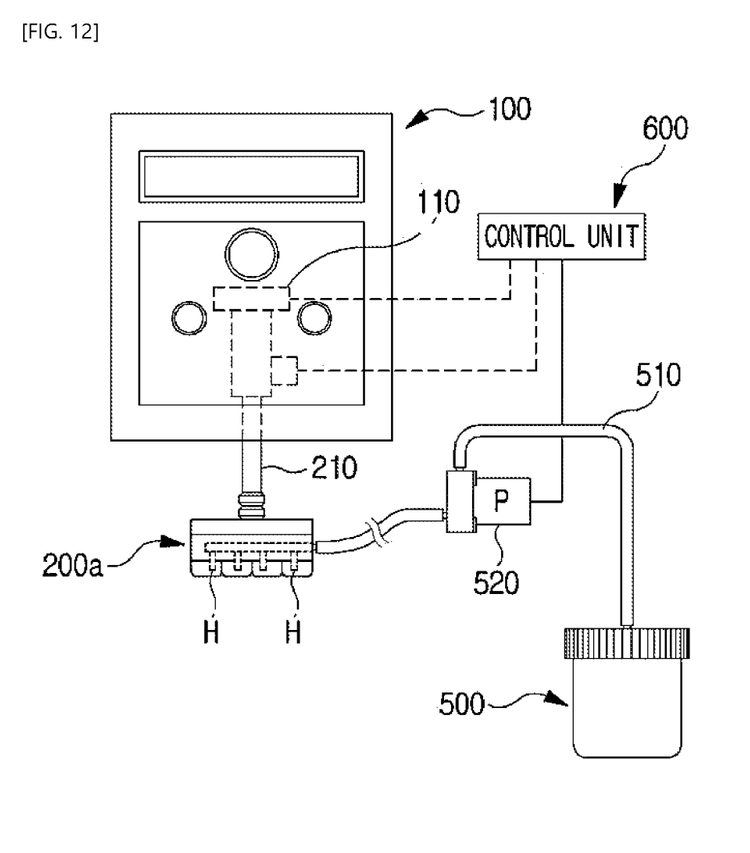

As illustrated in FIG. 12, a load cell 110 is installed in the main body 100.

In the present invention, the load cell is not an essential constituent element, but the load cell is connected to the present invention when the present invention is attached to the 'texture analyzer' and then used.

The load cell 110 senses a load value detected when the upper tooth probe 200a connected to a drive unit 210 comes into contact with the food, and the load cell 110 transmits the sensed load value to the display unit 700.

In the actual experiment, a Brookfield's 'texture analyzer' having a model name of 'CT-3' is used, but it is not necessarily limited thereto. Any device may be used if the device uses artificial teeth to reproduce the mastication and senses the load value generated by contact with food.

The following effects may be implemented by the previously filed invention.

First, it is possible to implement the mastication of the food with a degree of deformation similar to a high degree of deformation according to the mastication of the food performed in an oral cavity, and as a result, there is an advantage of measuring textural characteristics generated during the actual mastication of the food.

Second, there is an advantage of helping to implement the desired food through the load value graph over time.

Third, through the load value graph over time, there is an advantage of providing, in real-time, a load value generated at the time of initial mastication and a load value generated when the food is no longer deformed.

Fourth, there is an advantage in that sufficient data may be provided through the graph illustrating the load value over time during the research on the food and the food having desired physical properties may be developed by using the present invention during the development on the food. There is an advantage in that the load value generated in each mastication cycle is displayed in real-time, which helps an operator to understand the physical properties of the food.

Fifth, there is an advantage in that water and artificial saliva are supplied at a preset temperature, thereby sufficiently applying the environment of the human oral cavity.

Sixth, according to the present invention, the food, which is masticated with a high degree of deformation, is moved back to the position set before the mastication after the mastication is performed every time, such that the repeated mastication action actually occurring in the oral cavity is reproduced, and thus there is an advantage in that a continuous change in physical properties generated during the mastication of the food may be measured.

Seventh, the saliva in the oral cavity is effective when the continuous mastication is performed on the food, and there is an advantage in that the role of the saliva in the oral cavity, which acts on the physical properties during the mastication, is reproduced by the repeated mastication and the injection of the artificial saliva.

However, the invention previously filed by the present applicant relates to a system for reproducing the mastication when a person actually masticates the food. Unlike the actual human mastication, the invention has a limitation in precisely analyzing characteristics of the food.

In addition, although a configuration is disclosed to prevent a part of the food from being withdrawn during the mastication of the food, there is still a limitation in masticating the food having the same volume during the repeated reproduction.

Therefore, an object of the present invention is to more precisely analyze the characteristics of the food itself rather than to reproduce the actual human mastication. To this end, the present invention intends to consistently and repeatedly reproduce the mastication of the food having the same volume.

To this end, the present invention intends to more precisely analyze the characteristics of the food by newly modifying the structure of the previously filed invention including the upper tooth probe 200a and the temperature maintaining unit 300.

Hereinafter, the present invention will be specifically described.

Figure 4:
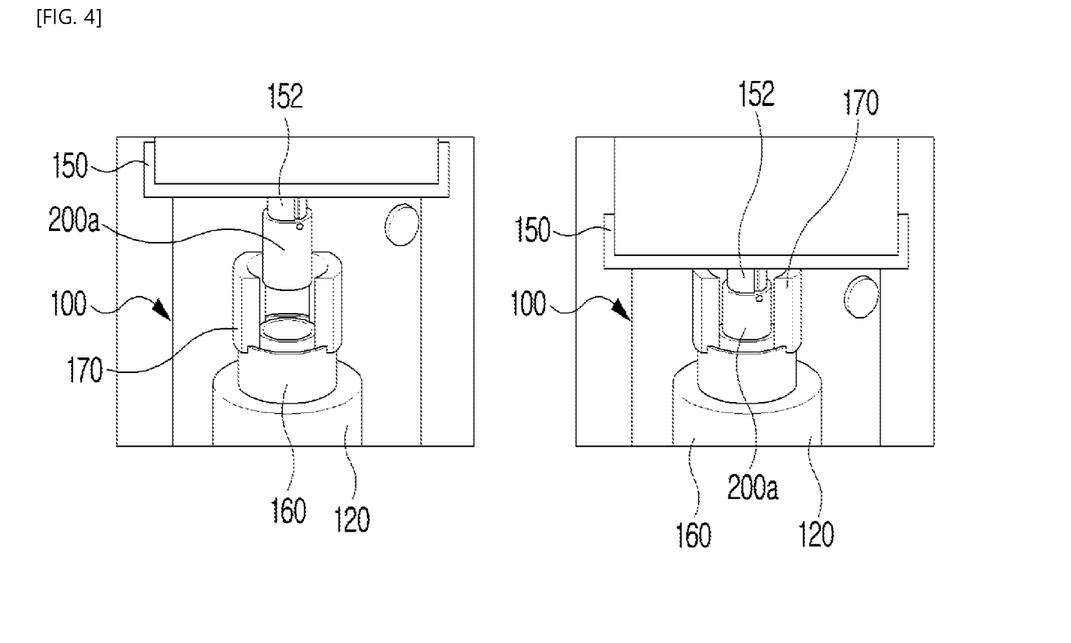
FIGS. 4 and 5 are photographs illustrating a state in which the present invention is fastened to a 'texture analyzer' which is a device used in the related art.
Figure 5:
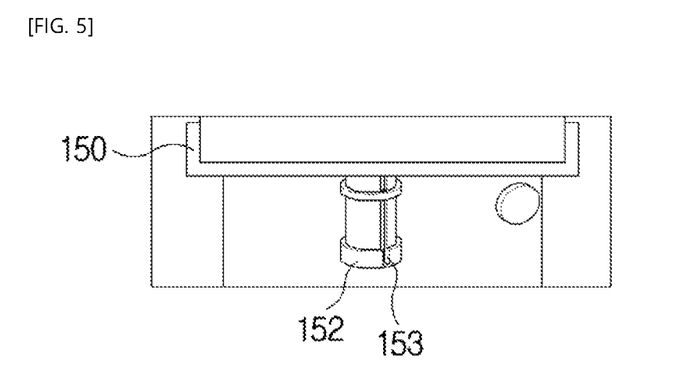

FIGS. 4 and 5 are actual photographs illustrating a state in which the present invention is fastened to the invention filed by the present applicant and illustrated in FIG. 3 or to the 'texture analyzer' used in the related art.

Figure 6:
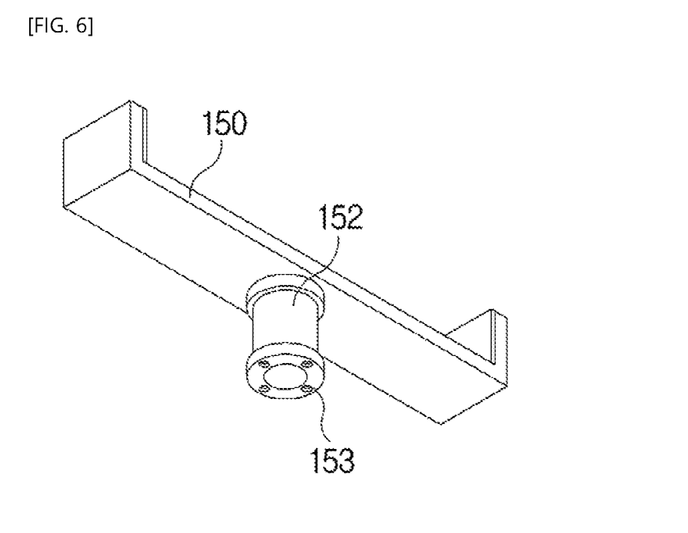
FIG. 6 is an actual photograph of a partial configuration view of the present invention.

FIG. 6 is a photograph of a fixing unit 150 which is a constituent element according to the present invention.

Figure 7:
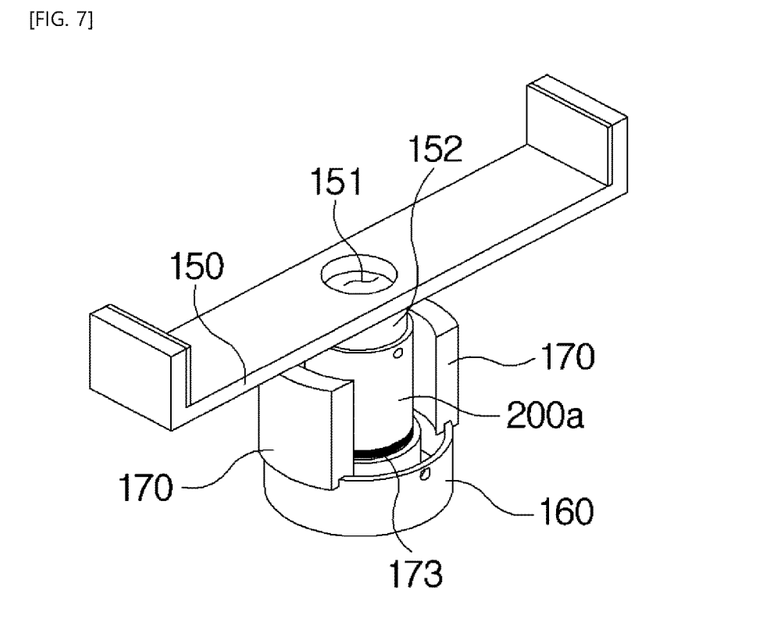
FIG. 7 is an actual photograph illustrating a state in which some constituent elements according to the present invention are fastened.

FIG. 7 is an actual photograph illustrating a state in which the fixing unit 150, a cylindrical probe 200a, and a food sample cup 160 are fastened.

The present invention broadly includes the fixing unit, the cylindrical probe, the food sample cup, and position fixing guides.

As illustrated, the fixing unit 150 is fixed to the main body 100 (the texture analyzer used in the related art) and the fixing unit 150 has, at a center thereof, a predetermined guide hole 151, and has a probe guide member 152 that has a predetermined space therein and extends downward.

The fixing unit 150 is fixed to the main body 100.

Various coupling methods may be applied. However, it is possible to apply any coupling configuration such as a configuration in which an adhesive component is provided on inner surfaces of portions bent upward from both ends of the fixing unit 150 to maintain coupling force with the main body 100 fastened to the fixing unit 150 so that a user may easily fasten the fixing unit 150 depending on the type of main body 100, or a configuration that may be fixed even by a frictional force.

Of course, the fixing unit 150 may be fastened to the main body 100 by bolting.

The guide hole 151 having a predetermined depth is formed at the center of the fixing unit 150. The drive unit moves upward and downward along the guide hole 151.

The drive unit 210 is not a constituent element essential to the present invention, but the drive unit 210 may be structured to be slidingly moved upward and downward, as illustrated in FIG. 3. A motor capable of moving the drive unit 210 upward and downward may be installed in the main body 100.

In addition, the control unit will be generally required when the present invention is coupled to the actual texture analyzer and then used. When the motor is operated by the control unit 600, the drive unit 210 is moved upward and downward based on a signal thereof to masticate the food provided on the food sample cup 160.

Meanwhile, the fixing unit 150 has the probe guide member 152 having a predetermined space and extending downward.

The drive unit 210 is moved upward and downward along the interior of the probe guide member 152, and the cylindrical probe 200a to be described below is moved upward and downward while surrounding the exterior of the probe guide member 152.

Figure 8:
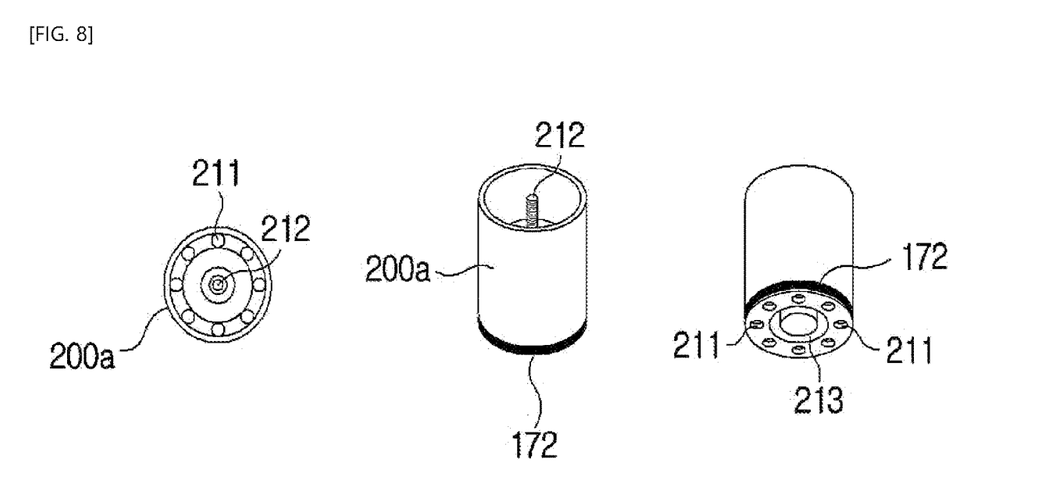
FIG. 8 is an actual photograph of a cylindrical probe which is a constituent element according to the present invention.

Meanwhile, the cylindrical probe has multiple holes formed on a lower surface thereof to extract a part of the food based on a degree of compression at the time of compressing the food as the cylindrical probe is moved upward and downward while surrounding the probe guide member 152.

FIG. 8 is an actual photograph of the cylindrical probe which is a constituent element according to the present invention.

The cylindrical probe 200a is connected to the drive unit 210 which extends to be connected to the present invention later along the guide hole 151.

The load cell 110 is connected to the drive unit 210 and senses the load value detected when the cylindrical probe 200a connected to the drive unit 210 comes into contact with the food, and the load cell 110 transmits the sensed load value to the display unit 700 that may be operated actually in conjunction with the present invention.

The cylindrical probe 200a is configured to surround the probe guide member 152.

The cylindrical probe 200a is moved upward and downward by the operation of the drive unit 210 in the state in which the cylindrical probe 200a surrounds the probe guide member 152.

Meanwhile, the multiple holes 211 are formed in the lower surface of the cylindrical probe 200a to extract a part of the food based on a degree of compression at the time of compressing the food.

This operational relationship will be described below.

The food, which is an experimental object, is placed on the food sample cup 160 to be described below, the food is compressed as the cylindrical probe 200a is moved downward, and a part of the food is extracted upward through the multiple holes 211 formed on the lower surface of the cylindrical probe 200a based on the degree of compression.

In the related art, because a part of the food is extracted to the outside at the time of compressing the food, a volume of the food is not constant when the food is compressed again, and as a result, it is impossible to accurately measure the physical properties of the food.

At the same position facing the multiple holes 211 and the lower surface of the probe guide member 152, a part of the food extracted upward through the holes 211 is captured by the holes 211 and the lower surface of the probe guide member 152.

The extracted food is positioned between the holes 211 and the lower surface of the probe guide member 152.

Further, in order to masticate the food again, the food is extracted downward again along the holes 211 when the cylindrical probe 200a is moved upward, such that the food is positioned on the food sample cup 160.

Further, the cylindrical probe 200a, which has been moved upward, is moved downward again to masticate the food having the volume equal to the volume when the food is compressed. As a result, it is possible to more accurately measure the physical properties of the food.

Of course, the food may be deformed again, that is, broken again as the cylindrical probe 200a moves upward and comes into contact with the lower surface of the probe guide member 152.

As illustrated in FIG. 8, the cylindrical probe 200a is opened at an upper side thereof, and the multiple holes 211 are formed to be spaced apart from one another at predetermined intervals along a circumference of the lower surface.

In addition, a connector 212 having a predetermined length is formed in the cylindrical probe 200a, and multiple screw threads are formed on an outer circumferential surface of the connector 212 so that the connector 212 may be connected to the drive unit 210.

The cylindrical probe 200a has an internally dual structure, and a predetermined space is formed between an outer wall of the cylindrical probe 200a and the connector 212 having the multiple screw threads and the predetermined length. The food extracted through the holes 211 is placed in the space.

Figure 9:
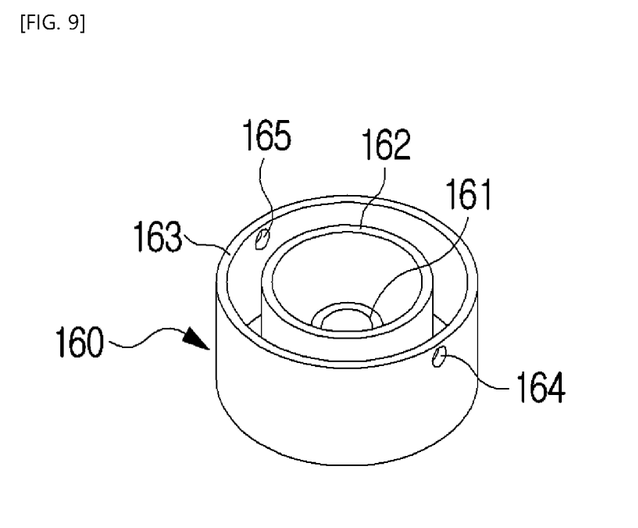
FIG. 9 is an actual photograph of a food sample cup which is a constituent element according to the present invention.

Meanwhile, the food sample cup is configured to have a space in which the food may be placed, and the food sample cup is positioned below the cylindrical probe.

As illustrated in FIG. 9, the food sample cup is seated on a base and has a space in which the food may be placed.

The structure of the food sample cup 160 will be described below in more detail.

A first cylinder 161, a second cylinder 162, and a third cylinder 163, which have different radii, are sequentially formed in a radial direction from the center thereof with the opened upper side thereof.

The food is placed between a partition wall of the first cylinder 161 and a partition wall of the second cylinder 162, and water having a preset temperature is supplied between the partition wall of the second cylinder 162 and a partition wall of the third cylinder 163.

A water supply hole 164 and a water discharge hole 165 are formed to face each other in an outer wall of the third cylinder 163 to supply the water having a predetermined temperature.

A height of the partition wall of the first cylinder 161 is smaller than a height of the second cylinder 162 and a height of the third cylinder 163.

Meanwhile, a predetermined inlet hole 213 is circumferentially formed in the lower surface of the cylindrical probe 200a in an internal height direction of the cylindrical probe 200a so that the outer wall of the first cylinder 161 may be inserted into the inlet hole 213 as the cylindrical probe 200a is moved downward and is inserted into the center of the first cylinder 161.

That is, as illustrated, the predetermined inlet hole 213 is circumferentially formed in the lower surface of the cylindrical probe 200a in the height direction along the interior of the cylindrical probe 200a.

The food is placed in the interior between the first cylinder 161 and the second cylinder 162, and the mastication is performed on the food as the cylindrical probe 200a is moved downward and the partition wall of the first cylinder 161 is inserted into the inlet hole 213.

In this case, a part of the food is extracted upward along the multiple holes 211 formed in the lower portion of the cylindrical probe 200a.

In the related art, there is no mastication device having the multiple holes 211. For this reason, there is a limitation in measuring the physical properties of the food according to the repeated mastication.

That is, it is important to repeatedly reproduce the mastication of the food having the same volume at the time of measuring the physical properties of the food during the repeated mastication of the food. To this end, the present invention is implemented so that the food having the same volume may be consistently and repeatedly masticated by means of the multiple holes 211.

When the present invention is coupled to the texture analyzer used in the related art, the present invention is suitable to observe a change in physical properties according to the repeated mastication of the food having various physical properties and textural characteristics, and the present invention may measure paste food, semisolid food, and liquid food as well as solid food by means of the multiple holes 211, as described above.

After the mastication is performed every time, the food, which is masticated with a high degree of deformation, is moved back to the position set before the mastication, such that the repeated mastication action actually occurring in the oral cavity is reproduced, and thus there is an advantage in that a continuous change in physical properties generated during the mastication of the food may be measured.

Figure 10:
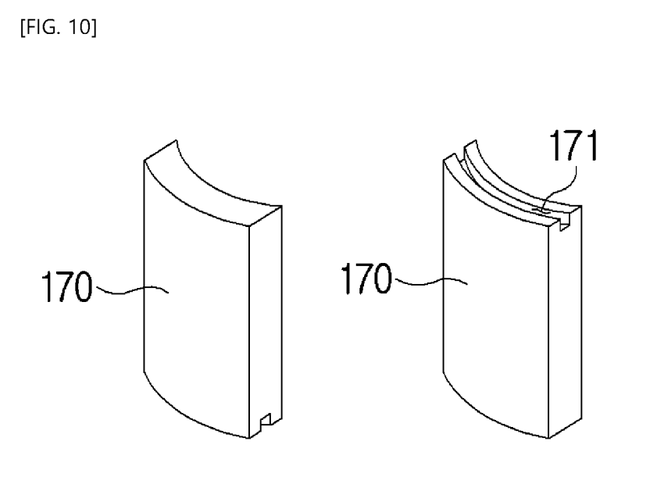
FIG. 10 is an actual photograph of a position fixing guide which is a constituent element according to the present invention.

Meanwhile, multiple position fixing guides are configured to be positioned between the fixing unit and the food sample cup.

The multiple position fixing guides 170 are positioned between the fixing unit 150 and the food sample cup 160 to prevent the food sample cup 160 from being moved when the cylindrical probe 200a is moved upward after the food is compressed.

That is, the multiple position fixing guides 170 serve to prevent the food sample cup 160 from being lifted when the cylindrical probe 200a is moved upward to masticate the food again after the food is masticated once.

To this end, the position fixing guide 170 has a predetermined curved shape, and a fitting hole 171, which corresponds to the shape of the outer wall of the third cylinder 163, is formed in a lower surface of the position fixing guide 170 so that the position fixing guide 170 may be fitted with the outer wall of the third cylinder 163.

The position fixing guide 170 entirely has a curved shape. An upper surface of the position fixing guide 170 is flat, and the fitting hole 171 having a predetermined depth is formed in the lower surface of the position fixing guide 170 so that the position fixing guide 170 may be fitted with the outer wall of the third cylinder 163.

The position fixing guides 170 prevents the food sample cup 160 from being lifted, thereby enabling an accurate experiment to be performed.

Meanwhile, a first O-ring 172 is formed on a lower outer circumferential surface of the cylindrical probe 200a, and a second O-ring 173 is also formed on a lower outer circumferential surface of the probe guide member 152, thereby preventing the food from being discharged to the outside.

Hereinafter, an operational relationship in the case in which the present invention is used by being coupled to the texture analyzer used in the related art will be described.

Referring back to FIG. 3, in the case in which the present invention is used by being coupled to the texture analyzer, a control unit 600 is provided to operate the drive unit 210, sense a load measured by the load cell, and store a preset degree of deformation of the food placed on the food sample cup 160 as the cylindrical probe 200a is moved downward, and the control unit 600 moves the cylindrical probe 200a downward at a preset speed and by a predetermined number of times to masticate the food.

That is, the control unit 600 transmits and receives operational signals to/from the motor connected to the drive unit 210 and controls the operation of the cylindrical probe 200a to move the drive unit 210 upward and downward.

In addition, in the case in which the present invention is used by being coupled to the texture analyzer used in the related art, a constant-temperature bath 400 is provided, as illustrated in FIG. 3. A signal is transmitted to a heating source 410 installed in the constant-temperature bath 400 to adjust a temperature of the water to a preset temperature, such that the water having a preset temperature is supplied to the water supply hole 164 formed in the outer wall of the third cylinder 163.

In addition, a signal is transmitted to an artificial saliva pump 520 installed in an artificial saliva supply unit 500, such that the artificial saliva is supplied to an artificial saliva supply port formed in the probe guide member 152.

Particularly, the artificial saliva is supplied by 1.45 ml/min to the artificial saliva pump 520, but it is apparent that the rate may be variously changed depending on experimental environments.

Figure 11:
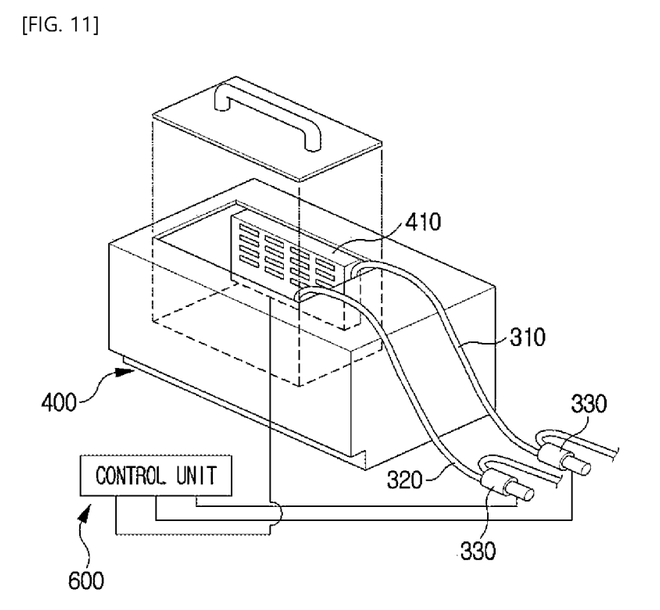
FIGS. 11 and 12 are partial configuration views of the invention filed by the present applicant.

In order to help understand the various structures, FIGS. 11 and 12 illustrating the invention previously filed by the present applicant will be referenced.

Meanwhile, the control unit 600 senses a load measured by the load cell 110, and particularly, the control unit 600 consistently senses a load value generated by the contact with the food.

The sensed load value is displayed as a graph over time on the display unit 700.

In addition, the operator allows the control unit 600 to store in advance a preset degree of deformation of the food F placed on the food sample cup when the cylindrical probe 200a is moved downward.

Figure 13:
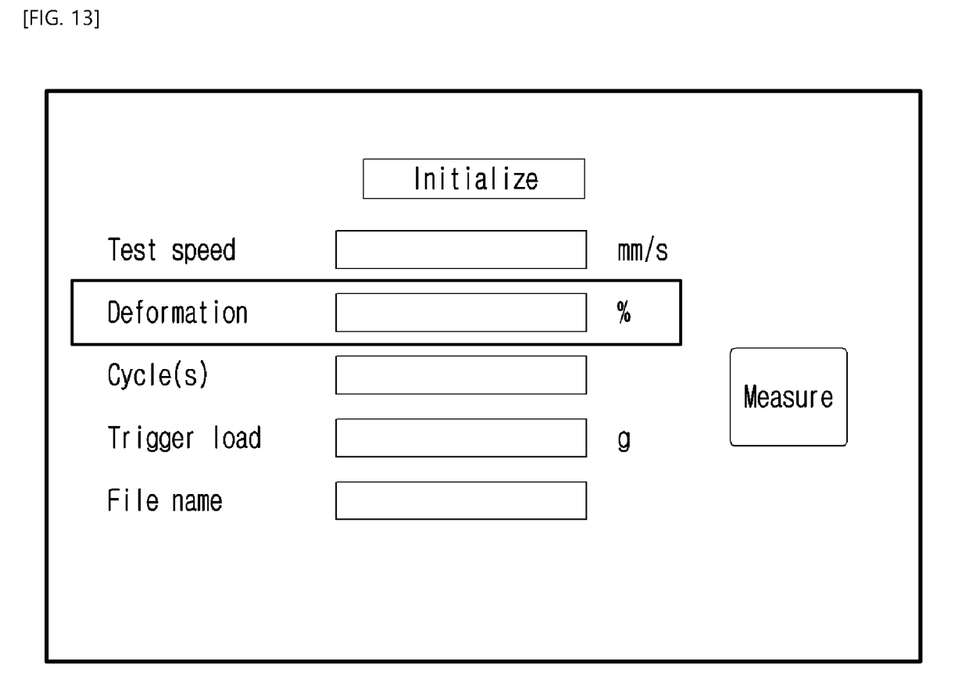
FIGS. 13 to 16 are views illustrating screens displayed on a display unit and implemented by a control unit in a case in which the present invention is coupled to the texture analyzer in the related art and then used.

FIG. 13 illustrates a screen implemented by the control unit 600 and displayed on the display unit 700. As illustrated, the operator inputs in advance a value of a degree of deformation.

The preset degree of deformation of the food means a degree of compression of food desired by the operator.

The control unit 600 is connected to the load cell 110 and consistently receives the load value sensed when the cylindrical probe 200a moves downward and comes into contact with the food F placed on the food sample cup 160.

As described above, the operator allows the control unit 600 to store in advance the degree of deformation of the food, that is, the degree of compression of the food. The drive unit 210 operates by the degree of deformation stored in advance, such that the cylindrical probe 200a compresses the food.

As described below, the degree of deformation of the food stored in advance by the user may be implemented as a distance between the cylindrical probe 200a and the base 120.

The control unit 600 receives the load value sensed in real-time by the load cell 110 while the food is compressed. The load value is shown to the operator in a graph on the display unit 700 to be described below.

Meanwhile, the control unit 600 moves the cylindrical probe 200a downward at a preset speed and by a preset number of times to masticate the food.

Figure 14:
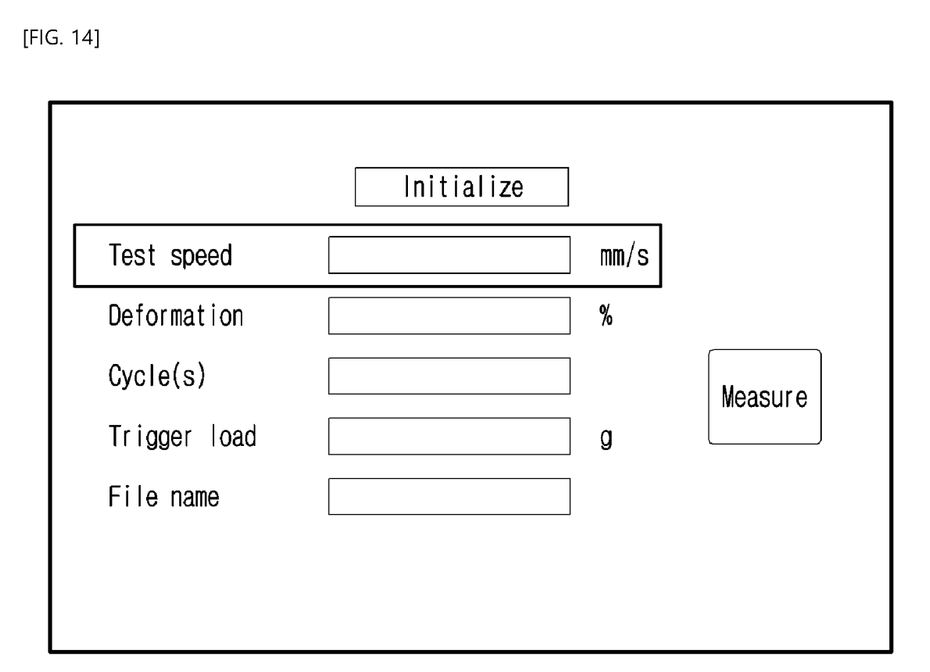
Figure 15:
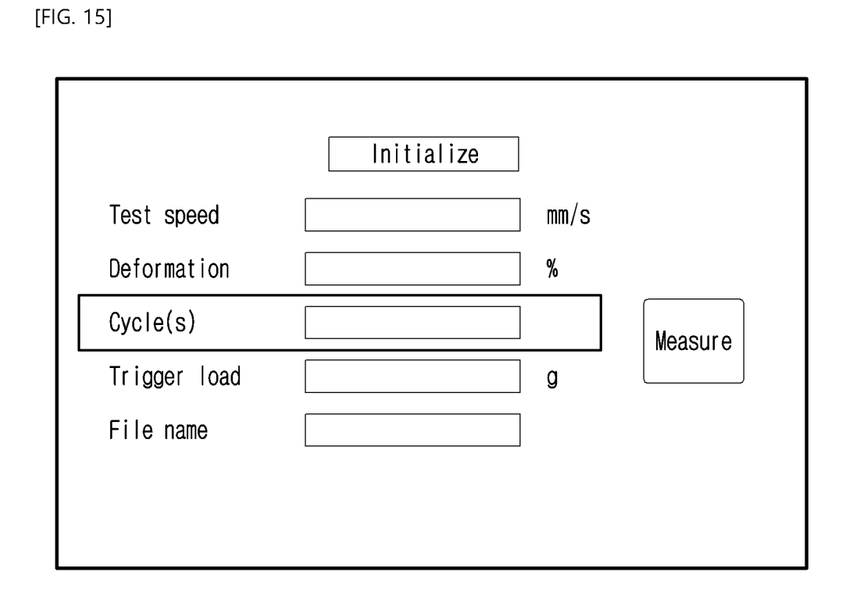

That is, as illustrated in FIGS. 14 and 15, the operator may input in advance the speed of the drive unit 210 and the cycle which is the number of times of the mastication.

With the display unit 700 implemented by the control unit 600, the operator may input in advance a speed at which the drive unit 210 moves upward and downward.

A maximum speed may be set to, but not necessarily limited to, 3 mm/s.

In addition, the operator may store in advance the number of times of the mastication of the food by the cylindrical probe 200a, that is, the number of cycles. The number of times of the mastication is determined depending on the stored number of cycles. The graph representing the time and the load value according to the number of cycles is shown to the operator through the display unit 700.

Meanwhile, in the case in which the present invention is used by being coupled to the texture analyzer used in the related art, the display unit 700 is configured to be used in conjunction with the texture analyzer.

The display unit 700 means a general monitor and is connected to the main body 100 and the control unit 600, respectively. The display unit 700 displays the graph representing the time according to the mastication and the load measured by the load cell 110. With the display unit 700, the speed of the drive unit 210, the number of times of the mastication, and the degree of deformation may be inputted.

That is, for example, assuming that the number of cycles, which is the number of times of the mastication, is 5, the display unit 700 displays the time according to the respective cycles and the load value sensed by the load cell 110 over time. This operation is implemented as the cylindrical probe 200a moves downward by the preset number of times in accordance with the preset degree of deformation.

Figure 16:
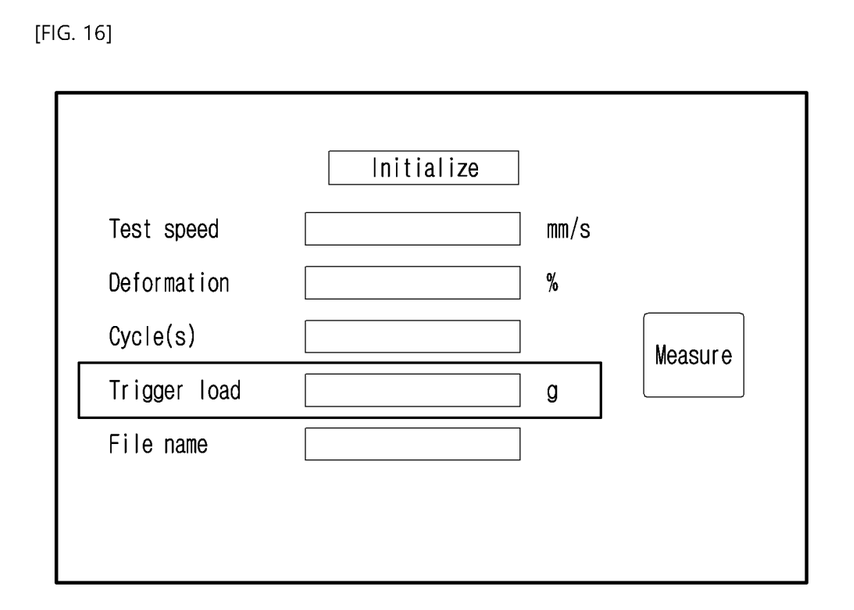

Meanwhile, the control unit 600 stores in advance a trigger load value detected when the cylindrical probe 200a comes into contact with the food.

When the trigger load value is measured by the load cell as the cylindrical probe 200a is moved downward by the operation of the drive unit and comes into contact with the food, the control unit 600 allows the display unit 700 to display the graph representing the time according to the mastication and the load detected by the load cell from a measurement point in time.

FIG. 16 illustrates the trigger load value that may be stored in advance by the user in the display unit 700 that operates in conjunction with the control unit 600.

The trigger load value means a load value detected when the cylindrical probe 200a moves downward and initially comes into contact with the food placed on the food sample cup 160.

The trigger load value may be inputted in advance by the user through various experiments. In the case of food having weak materials, that is, soft food, the trigger load value will be smaller. The harder the food, the larger the trigger load value will be stored in advance.

A maximum trigger load value may be set to, but not necessarily limited to, 10,000 g.

When the load value corresponding to the trigger load value is detected by the load cell 110, the control unit 600 detects that the cylindrical probe 200a comes into contact with the food placed on the food sample cup 160.

The cylindrical probe 200a is moved downward from this point in time so that the degree of deformation corresponds to the preset degree of deformation.

When the trigger load value is measured by the load cell 110 as the cylindrical probe 200a is moved downward by the operation of the drive unit 210 and comes into contact with the food, the control unit 600 allows the display unit 700 to display the graph representing the time according to the mastication and the load detected by the load cell 110 from a measurement point in time.

That is, when the load corresponding to the trigger load value is detected by the control unit 600, the mastication is performed by the preset number of cycles, and the load generated when the mastication of the food is performed for each cycle is implemented as a graph.

The control unit 600 stores in advance a height of the base 120 and stores in advance a distance between the cylindrical probe 200a and the food sample cup 160 before the cylindrical probe 200a moves downward. The control unit 600 senses a position of the cylindrical probe 200a at a point in time at which the trigger load value stored in advance is detected. The control unit 600 moves the cylindrical probe 200a downward to the position corresponding to the preset degree of deformation of the food.

The height of the base 120 is displayed on the display unit 700 in real-time by a sensor installed in the base 120 and configured to detect the height.

An adjustment screw configured to adjust the height of the base 120 is provided in front of the base 120, the motor may be installed to be adjacent to the adjustment screw, a signal generated by a rotation of the motor or a rotation of the adjustment screw is transmitted to the main body 100 or the control unit 600, and the height of the base 120 is displayed on the display unit 700 based on a value of the signal.

Of course, the height of the base 120 may be displayed on the display unit 700 in various ways in addition to the above-mentioned method.

In addition, a height of the cylindrical probe 200a may also be stored in advance by the user, a height of an end of the drive unit 210 connected to the cylindrical probe 200a may also be stored in advance by the user, the motor, which may operate in conjunction with the drive unit 210, may also be installed at an upper end of the drive unit 210 in the main body 100, a rotation signal of the motor is transmitted to the main body 100 or the control unit 600, and the height according to the rotation is transmitted, such that the height of the end of the cylindrical probe 200a may be displayed on the display unit 700.

Figure 17:
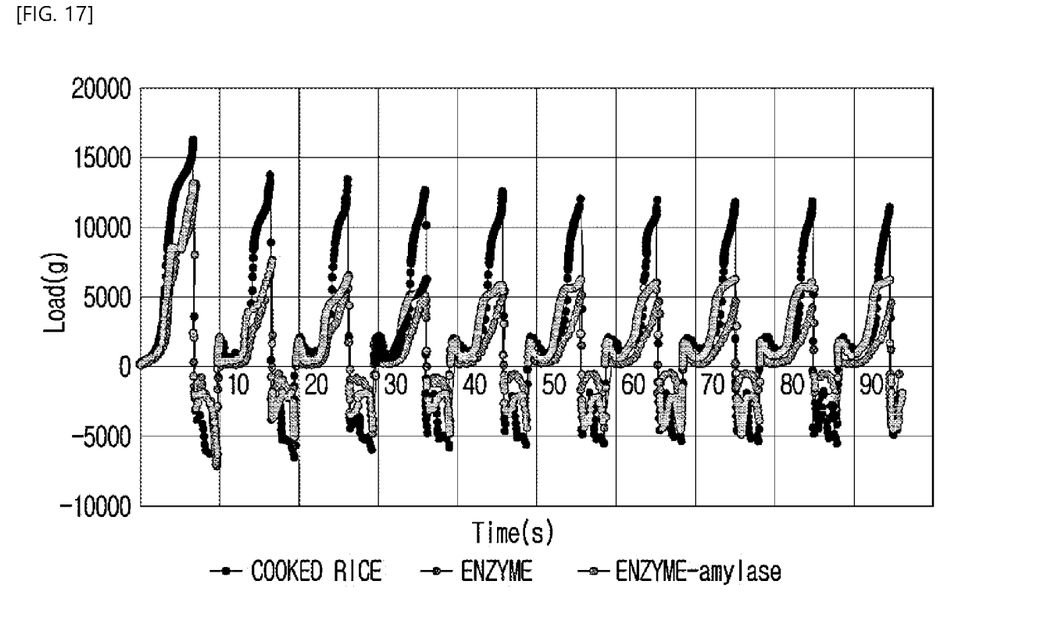
FIG. 17 is a graph illustrating load values detected by a load cell in accordance with deformation of food when the mastication is repeated 10 times by using the present invention.

The height of the cylindrical probe 200a and the height, that is, the distance between the cylindrical probe 200a and the food sample cup 160 may also be displayed on the display unit 700 in various ways in addition to the above-mentioned method. Meanwhile, FIG. 17 illustrates load values detected by the load cell in accordance with deformation of food when the mastication is repeated 10 times by using the present invention.

The parts indicated in blue indicate a graph in a case in which cooked rice is used, and the parts indicated in red indicate a graph in a case in which enzyme (artificial saliva) is supplied.

In the graph in the case in which the cooked rice without enzyme is used and the graph in the case in which the cooked rice with enzyme is used, the rising parts indicate the load values generated in the state in which the cylindrical probe 200a compresses the cooked rice, and the lowering parts indicate the parts in which the cylindrical probe 200a moves upward to perform the mastication again after the preset degree of deformation is completed.

In this case, there are a case in which a positive (+) load value is generated, and a case in which a negative (−) load value is generated. The positive (+) load value refers to the load value generated when the cylindrical probe 200a compresses the food while moving downward. The negative (−) load value refers to the load value sensed by the cylindrical probe 200a when the cylindrical probe 200a moves upward again and when the food extracted along the holes 211 moves downward again to the food sample cup 160 along the holes 211.

That is, the negative (−) value is generated when the load value is generated in the direction opposite to the direction in which the food is pressed.

The negative load value means a load value of the broken food. If the absolute value of the load value is large, it means that the mastication needs to be performed to further break the food. If the absolute value of the load value is small, it means that a degree to which the food is broken is high by one mastication.

Meanwhile, a so-called 'packing' state of the food may be ascertained by means of the illustrated graph.

The fundamental reason for ascertaining the degree of 'packing' in the present invention is that the volume of the food, which is an experimental object, may be maintained consistently.

That is, the food has pores formed between particles, and a hard substance and a paste substance will have different porosities.

In this case, the cylindrical probe 200*a* compresses the food while moving downward, the porosity is sufficiently reduced, and then a part of the food is extracted along the holes 211.

The gradient of the rising curve in the illustrated graph indicates the degree of 'packing' of the food. The rapidly rising curve may be determined that the food is closer to the solid than the paste to that extent food, and the slowly rising curve may be determined that the food is closer to the paste than the solid.

The rising curve in the illustrated graph includes a packing portion for reducing the porosity of the food, a portion in which a part of the food is extracted along the holes 211 after being packed, and a portion for consistently pressing the food while a part of the food is extracted.

Referring back to the illustrated graph, it can be seen that a reduction rate of a maximum load value for each cycle is smaller in the case in which the cooked rice without enzyme is used than the case in which the enzyme (artificial saliva) is inputted.

It can be seen that the reduction rate of the maximum load value for each cycle is smaller in the case in which the cooked rice without enzyme is used than the case in which the cooked rice with enzyme is used. That is, the cooked rice changes to the form of 'porridge' after the enzyme is added and the mastication is repeated 10 times, and the cooked rice changes to the form of 'rice cake' when the experiment is performed by using only the cooked rice.

Therefore, it is again proved that the enzyme needs to be added in addition to a supply of water having an appropriate temperature to simulate the environment in the oral cavity.

As described above, the present invention is a technology that may be applied to various application fields when the present invention is used by being coupled to the texture analyzer used in the related art, and the present invention is suitable for observing changes in physical properties in accordance with the repeated mastication of the food having various physical properties and textural characteristics.

The present invention makes it possible to observe the changes in physical properties caused by the repeated deformation of the food including several particles, the food in the form of paste, and the food containing jellies, liquids, and solids. The present invention may be used throughout the research and the food industry as a technology capable of being used as an alternative to sensory evaluation.

Hereinafter, a system for repeatedly measuring textural characteristics of food according to the present invention will be described.

As already described above, FIG. 4 is an actual photograph illustrating a state in which some constituent elements according to the present invention are attached to the invention filed by the present applicant.

The present invention broadly includes the main body 100, the fixing unit 150, the cylindrical probe 200*a*, the food sample cup 160, the position fixing guide 170, the control unit 600, and the display unit 700.

The load cell 110 is installed in the main body 100, and the main body 100 includes the base 120 having a predetermined height.

FIG. 12 is a schematic view illustrating a state in which the load cell 110 employed in the present invention is installed with the invention previously filed by the present applicant.

The load cell 110 senses the load value detected when the cylindrical probe 200*a* connected to the drive unit 210 to be described below comes into contact with the food, and the load cell 110 transmits the sensed load value to the display unit 700.

Like the previously filed invention, in the present invention, the base 120 having the predetermined height is installed in front of the main body 100, as illustrated in FIGS. 3 and 4.

The height of the base 120 is adjusted by the operation of the screw that may move the base 120 upward and downward, and the food sample cup 160 to be described below is seated on the base 120.

The motor may be installed in the base 120 so that the height of the base 120 may be sensed when the base 120 is moved upward and downward by the operation of the screw. The height of the base 120, which varies in accordance with the rotation of the motor, may be transmitted in real-time to the display unit 700.

Of course, various structures may be employed in the present invention in addition to the above-mentioned configuration as long as the structure may transmit the height of the base 120 to the display unit 700.

Meanwhile, FIG. 4 is an actual photograph illustrating a state in which the fixing unit 150, which is a constituent element according to the present invention, is installed in the main body 100, FIG. 5 is an actual photograph of the fixing unit 150, and FIG. 6 is an actual photograph illustrating a state in which the fixing unit 150, the cylindrical probe 200*a*, and the food sample cup 160 are fastened.

As illustrated in FIGS. 5, 6, and 7, the fixing unit 150 is fixed to the main body 100 and the fixing unit 150 has, at a center thereof, a predetermined guide hole 151, and has a probe guide member 152 that has a predetermined space therein and extends downward.

The fixing unit 150 is fixed to the main body 100. Various coupling methods may be applied. However, it is possible to apply any coupling configuration such as a configuration in which an adhesive component is provided on inner surfaces of portions bent upward from both ends of the fixing unit 150 to maintain coupling force with the main body 100 fastened to the fixing unit 150 so that a user may easily fasten the fixing unit 150 depending on the type of main body 100, or a configuration that may be fixed even by a frictional force.

Of course, the fixing unit 150 may be fastened to the main body 100 by bolting.

The guide hole 151 having a predetermined depth is formed at the center of the fixing unit 150. The drive unit moves upward and downward along the guide hole 151.

The drive unit 210 may be structured to be slidingly moved upward and downward, as illustrated in FIG. 12. The motor capable of moving the drive unit 210 upward and downward may be installed in the main body 100.

When the motor is operated by the control unit 600 to be described below, the drive unit 210 is moved upward and downward based on the signal of the motor to masticate the food on the food sample cup 160.

Meanwhile, the fixing unit 150 has the probe guide member 152 having a predetermined space and extending downward.

The drive unit 210 is moved upward and downward along the interior of the probe guide member 152, and the cylindrical probe 200*a* to be described below is moved upward and downward while surrounding the exterior of the probe guide member 152.

The invention claimed is:

1. A detachable device for repeatedly measuring textural characteristics of food, the device comprising:

a fixing unit having a probe guide member having, at a center thereof, a predetermined guide hole, having therein a predetermined space, and extending downward;
a cylindrical probe configured to move upward and downward while surrounding the probe guide member and having multiple holes formed in a lower surface thereof so that a part of food is extracted in accordance with a degree of compression at the time of compressing the food;
a food sample cup positioned below the cylindrical probe and having therein a space in which the food is placed;
multiple position fixing guides positioned between the fixing unit and the food sample cup;
wherein the cylindrical probe is opened at an upper side thereof, multiple holes are formed along a circumference of a lower surface of the cylindrical probe so as to be spaced apart from one another at predetermined intervals, and a connector having a predetermined length and having multiple screw threads formed on an outer circumferential surface thereof is formed in the cylindrical probe; and
wherein the food sample cup has a first cylinder, a second cylinder, and a third cylinder that have different radii and are formed sequentially in a radial direction from a center thereof with opened upper sides, the food is placed between the first cylinder and the second cylinder, water having a preset temperature is provided between the second cylinder and the third cylinder, and a water supply hole and a water discharge hole are formed in an outer wall of the third cylinder so as to face each other so that the water having the preset temperature is supplied.

2. The device of claim 1, wherein a predetermined inlet hole is circumferentially formed in the lower surface of the cylindrical probe in an internal height direction of the cylindrical probe so that an outer wall of the first cylinder is inserted into the inlet hole when the cylindrical probe is inserted into the center of the first cylinder.

3. The device of claim 1, wherein each of the multiple position fixing guides has a predetermined curved shape and has a fitting hole formed in a lower surface thereof and corresponding to a shape of the outer wall of the third cylinder so that the fitting hole is fitted with the outer wall of the third cylinder.

4. The device of claim 1, wherein a first O-ring is formed on a lower outer circumferential surface of the cylindrical probe, and a second O-ring is also formed on a lower outer circumferential surface of the probe guide member.

5. The device of claim 1, wherein an artificial saliva supply port for supplying artificial saliva is formed in the probe guide member in a height direction.

6. A system for repeatedly measuring textural characteristics of food, the system comprising:
a main body having a load cell installed therein, the main body including a base having a predetermined height;
a fixing unit fixed to the main body, having a probe guide member having, at a center thereof, a predetermined guide hole, having therein a predetermined space, and extending downward;
a cylindrical probe connected to a drive unit extending along the interior of the guide hole, the cylindrical probe being configured to move upward and downward while surrounding the probe guide member and having multiple holes formed in a lower surface thereof so that a part of food is extracted in accordance with a degree of compression at the time of compressing the food;
a food sample cup seated on the base and having therein a space in which the food is placed;
multiple position fixing guides positioned between the fixing unit and the food sample cup to prevent the food sample cup from moving when the cylindrical probe moves upward after the food is compressed;
a control unit configured to control an operation of the drive unit, sense a load measured by the load cell, store a preset degree of deformation of the food placed on the food sample cup as the cylindrical probe moves downward, and move the cylindrical probe downward at a preset speed and by a preset number of times to masticate the food;
a display unit configured to display a graph corresponding to the time according to the mastication and the load measured by the load cell;
wherein the cylindrical probe is opened at an upper side thereof, multiple holes are formed along a circumference of a lower surface of the cylindrical probe so as to be spaced apart from one another at predetermined intervals, and a connector having a predetermined length and having multiple screw threads formed on an outer circumferential surface thereof is formed in the cylindrical probe so as to be connected to the drive unit; and
wherein the food sample cup has a first cylinder, a second cylinder, and a third cylinder that have different radii and are formed sequentially in a radial direction from a center thereof with opened upper sides, the food is placed between the first cylinder and the second cylinder, water having a preset temperature is supplied between the second cylinder and the third cylinder, and a water supply hole and a water discharge hole are formed in an outer wall of the third cylinder so as to face each other so that the water having the preset temperature is supplied.

7. The system of claim 6, wherein a predetermined inlet hole is circumferentially formed in the lower surface of the cylindrical probe in an internal height direction of the cylindrical probe so that an outer wall of the first cylinder is inserted into the inlet hole when the cylindrical probe is moved downward and inserted into the center of the first cylinder.

8. The system of claim 6, wherein each of the multiple position fixing guides has a predetermined curved shape and has a fitting hole formed in a lower surface thereof and corresponding to a shape of the outer wall of the third cylinder so that the fitting hole is fitted with the outer wall of the third cylinder.

9. The system of claim 6, wherein a first O-ring is formed on a lower outer circumferential surface of the cylindrical probe, and a second O-ring is also formed on a lower outer circumferential surface of the probe guide member.

10. The system of claim 6, wherein an artificial saliva supply port for supplying artificial saliva is formed in the probe guide member in a height direction.

11. The system of claim 10, further comprising:
an artificial saliva supply unit configured to store a predetermined amount of artificial saliva and connected to the artificial saliva supply port through an artificial saliva supply line to supply the artificial saliva to the artificial saliva supply port,
wherein an artificial saliva pump is installed at one point of the artificial saliva supply line, and the artificial saliva pump is controlled by the control unit.

12. The system of claim 6, further comprising:
a constant-temperature bath configured to store a predetermined amount of water to supply and discharge the water having a preset temperature,
wherein a water supply line and a water discharge line are connected to the water supply hole and the water discharge hole, respectively, formed in the outer wall of the third cylinder, water pumps are installed in the water supply line and the water discharge line, respectively, and the water pumps are controlled by the control unit.

13. The system of claim 6, wherein the control unit stores in advance a trigger load value detected when the cylindrical probe comes into contact with the food, and when the trigger load value is sensed by the load cell by the contact with the food when the cylindrical probe is moved downward by an operation of the drive unit, the control unit displays, on the display unit, a graph corresponding the time according to the mastication from the sensing point in time and corresponding to a load detected by the load cell.

14. The system of claim 13, wherein the control unit stores in advance a height of the base and stores in advance a distance between the cylindrical probe and the food sample cup before the cylindrical probe moves downward, the control unit senses a position of the cylindrical probe at a point in time at which the trigger load value stored in advance is detected, and the control unit moves the cylindrical probe downward to a position corresponding to a preset degree of deformation of the food.

* * * * *